(12) United States Patent
Ebisawa

(10) Patent No.: US 8,371,693 B2
(45) Date of Patent: Feb. 12, 2013

(54) AUTISM DIAGNOSIS SUPPORT APPARATUS

(75) Inventor: Yoshinobu Ebisawa, Hamamatsu (JP)

(73) Assignee: National University Corporation Shizuoka University (JP)

( * ) Notice: Subject to any disclaimer, the term of this patent is extended or adjusted under 35 U.S.C. 154(b) by 133 days.

(21) Appl. No.: 13/074,606

(22) Filed: Mar. 29, 2011

(65) Prior Publication Data

US 2011/0242486 A1    Oct. 6, 2011

Related U.S. Application Data

(60) Provisional application No. 61/318,956, filed on Mar. 30, 2010.

(51) Int. Cl.
*A61B 3/14* (2006.01)
(52) U.S. Cl. .................. 351/206; 351/205; 351/210
(58) Field of Classification Search .......... 351/204–206, 351/209, 210
See application file for complete search history.

(56) References Cited

U.S. PATENT DOCUMENTS

| | | | |
|---|---|---|---|
| 7,533,989 B2 | 5/2009 | Ebisawa | |
| 7,963,652 B2 * | 6/2011 | Vertegaal et al. | 351/205 |
| 2009/0073381 A1 * | 3/2009 | Wheeler et al. | 351/206 |
| 2009/0196460 A1 * | 8/2009 | Jakobs et al. | 382/103 |

FOREIGN PATENT DOCUMENTS

WO    2007/023798    3/2007

OTHER PUBLICATIONS

Ami Klin, et al., "Visual Fixation Patterns During Viewing of Naturalistic Social Situations as Predictors of Social Competence in Individuals with Autism," Arch Gen Psychiatry, vol. 59, Sep. 2002, pp. 809-816.
Warren Jones, et al., "Absence of Preferential Looking to the Eyes of Approaching Adults Predicts Level of Social Disability in 2 Year-Old Toddlers with Autism Spectrum Disorder," Arch Gen Psychiatry, vol. 65, No. 8, Aug. 2008, pp. 946-954.

* cited by examiner

*Primary Examiner* — Huy K Mai
(74) *Attorney, Agent, or Firm* — Ostrolenk Faber LLP

(57) ABSTRACT

An autism diagnosis support apparatus 1 according to the present invention is an autism diagnosis support apparatus that detects a symptom of autism based on a state of a subject looking at a target, including: an eye-gaze point detection unit 2 that detects a line-of-sight direction of the subject looking at the target; a color camera 3 that takes an image of the target; a pupil position detection unit 4 that measures a pupil coordinate of the target; and a data analysis unit 7 that calculates a relationship between the line-of-sight direction of the subject and a pupil position of the target using the line-of-sight direction and the pupil coordinate and outputs the relationship along with the image of the target.

5 Claims, 5 Drawing Sheets

AUTISM DIAGNOSIS SUPPORT APPARATUS

Cross-Reference To Related Application

This application claims priority to Provisional Application Ser. No. 61/318,956 filed on Mar. 30, 2010, which is hereby incorporated by reference in its entirety.

BACKGROUND OF THE INVENTION

1. Field of the Invention

The present invention relates to an autism diagnosis support apparatus using a diagnostic of autism.

2. Related Background Art

Autism is a developmental disorder occurring in infants aged up to three, and one in 50 to 60 people develops autism and related disorders. Typical symptoms of autism include impaired communication due to inability to make eye contact, lack of emotional interaction due to an inability to imagine the feelings of others, and display of limited interests and behaviors.

Attempts have been made to improve social adjustment of autistic people by early autism diagnosis for early start of remedial education. For example, pediatricians and child psychiatrists have diagnosed autism by observing behaviors of infants and making an evaluation based on their behaviors. However, the shortage of specialists in such diagnosis approach makes early diagnosis practically difficult.

Other approaches to autism diagnosis under consideration include biological evaluation such as a specific serum molecular method. This diagnosis approach involves analyzing a patient's serum to identify the patient as healthy or autistic.

SUMMARY OF THE INVENTION

The above conventional diagnosis approaches, however, require a skilled diagnostician, and the diagnostic outcome tends to depend on a diagnostician due to the lack of objective diagnosis result. In addition, the biological evaluation requires blood collection from the patient and serum analysis, posing the problem that prompt diagnosis cannot be carried out.

The present invention has been made in view of the above inconveniences, and an object of the present invention is to provide an autism diagnosis support apparatus that allows for quick acquisition of highly reliable diagnostic data.

We have made keen examination to obtain findings that when an autistic person as a subject is required to communicate with others face to face, he/she looks at a body part such as a mouth rather than eyes more frequently than healthy people do. The present invention provides a system for diagnosing whether a subject has a symptom of autism from a difference between a time when the subject looks at eyes of an objective person (observed target) and a time when the subject looks at a different point.

An autism diagnosis support apparatus according to an aspect of the present invention is an autism diagnosis support apparatus that detects a symptom of autism based on a state of a subject looking at a target, including: a line-of-sight detection unit that detects a line-of-sight direction of the subject looking at the target; a camera that takes an image of the target; a pupil position detection unit that measures a pupil coordinate of the target; and a data analysis unit that calculates a relationship between the line-of-sight direction of the subject and a pupil position of the target using the line-of-sight direction and the pupil coordinate and outputs the relationship along with the image of the target.

DESCRIPTION OF THE PREFERRED EMBODIMENTS

Embodiment 1

An embodiment will be described of an apparatus which performs eye-gaze point detection for autism diagnosis in a medical examination for about 18-month old infants.

In this case, a minimum examination time and only one examination are desirable. In such a case, an eye-gaze point of an infant (a subject) is detected while a face of a mother (observed target) is captured to video signal and the image of the face is displayed on a display (a target which a subject looks face to face), or an eye-gaze point is detected while an image of the face of the mother video-captured immediately before the eye-gaze point detection is shown to the infant.

Figure 1:
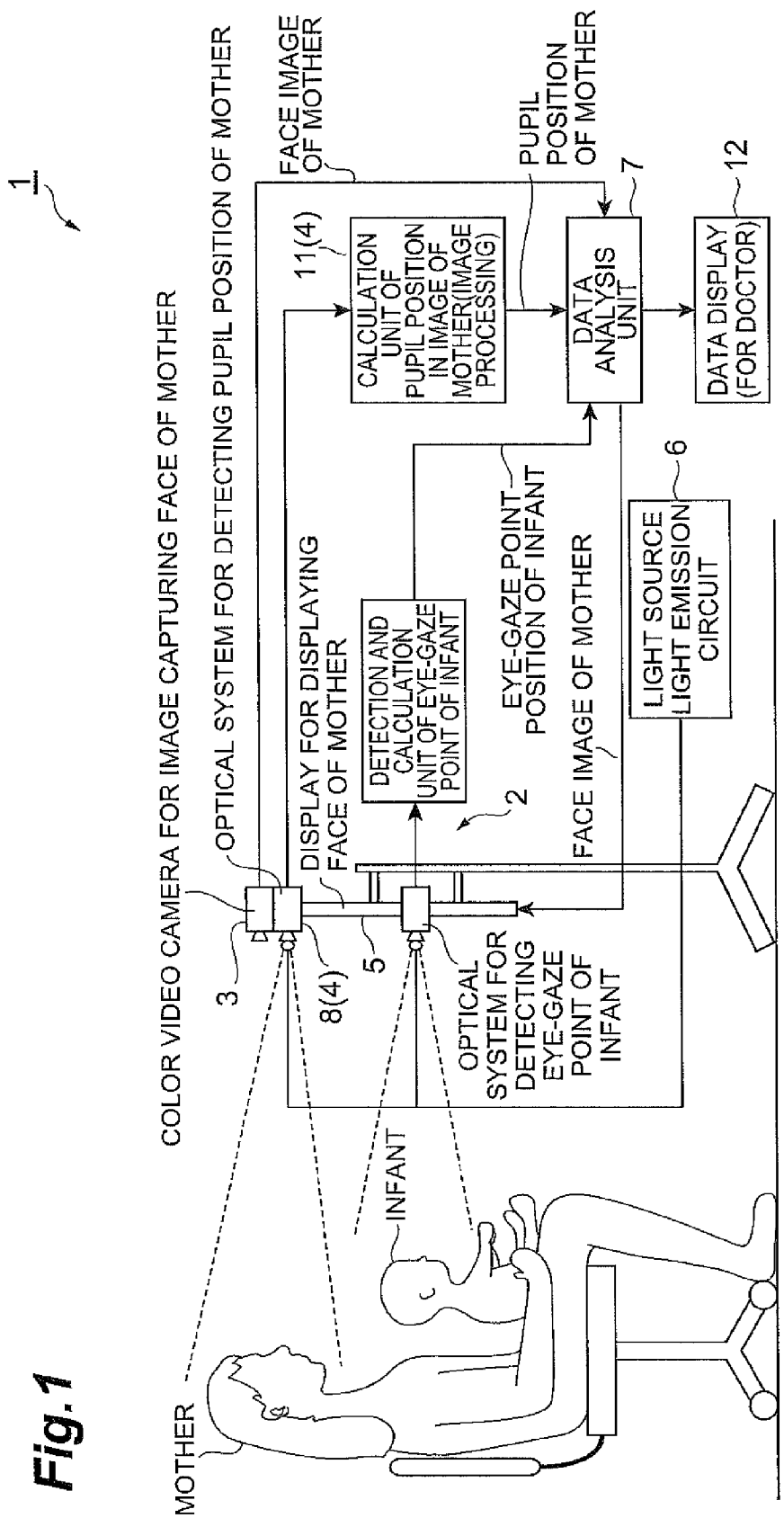
FIG. 1 is a schematic configuration diagram showing an entire configuration of an autistic infant diagnosis apparatus according to a first embodiment of the present invention.

For this purpose, a face or at least a part of a body of a mother or a closest person who rears the infant (hereinafter simply referred to as a mother) is displayed on a display that constitutes an apparatus of the present invention. To actually detect an eye-gaze point while showing a moving image to the infant, it is necessary to control movement of the infant to some extent so that the infant faces the display, and also comfort the infant. Thus, the eye-gaze point detection for autism diagnosis is desirably performed with the mother holding the infant on her lap (FIG. 1).

As described above, an autistic infant diagnosis apparatus requires an eye-gaze point detection device for determining whether an infant is looking at eyes of a mother. Thus, an autistic infant diagnosis apparatus 1 shown in FIG. 1 includes components described below. Specifically, the autistic infant diagnosis apparatus 1 includes an eye-gaze point detection unit 2 (a three-dimensional view-point measurement device described in U.S. Pat. No. 7,533,989 by this inventor may be used) that can measure an eye-gaze point of an infant in real time, a color camera 3 that takes an image of the face (or at least a part of the body) of a mother, a pupil position detection unit 4 (a pupil detection device and a pupil detection method described in International Publication No. WO 2007/023798 by this inventor may be used) for measuring space coordinates of the pupils of the mother in real time, a display 5 that displays an image of the mother, a light source light emission circuit 6, and a data analysis unit 7.

This system configuration enables immediate and easy quantification of a deviation of the eye-gaze point of the infant from the positions of the mother's eyes. It is very advantageous that the eye positions can be automatically and precisely detected while a face image is captured even when a pre-captured image of a person who is not necessarily the mother accompanying the infant in the medical examination is captured and displayed.

Figure 2:
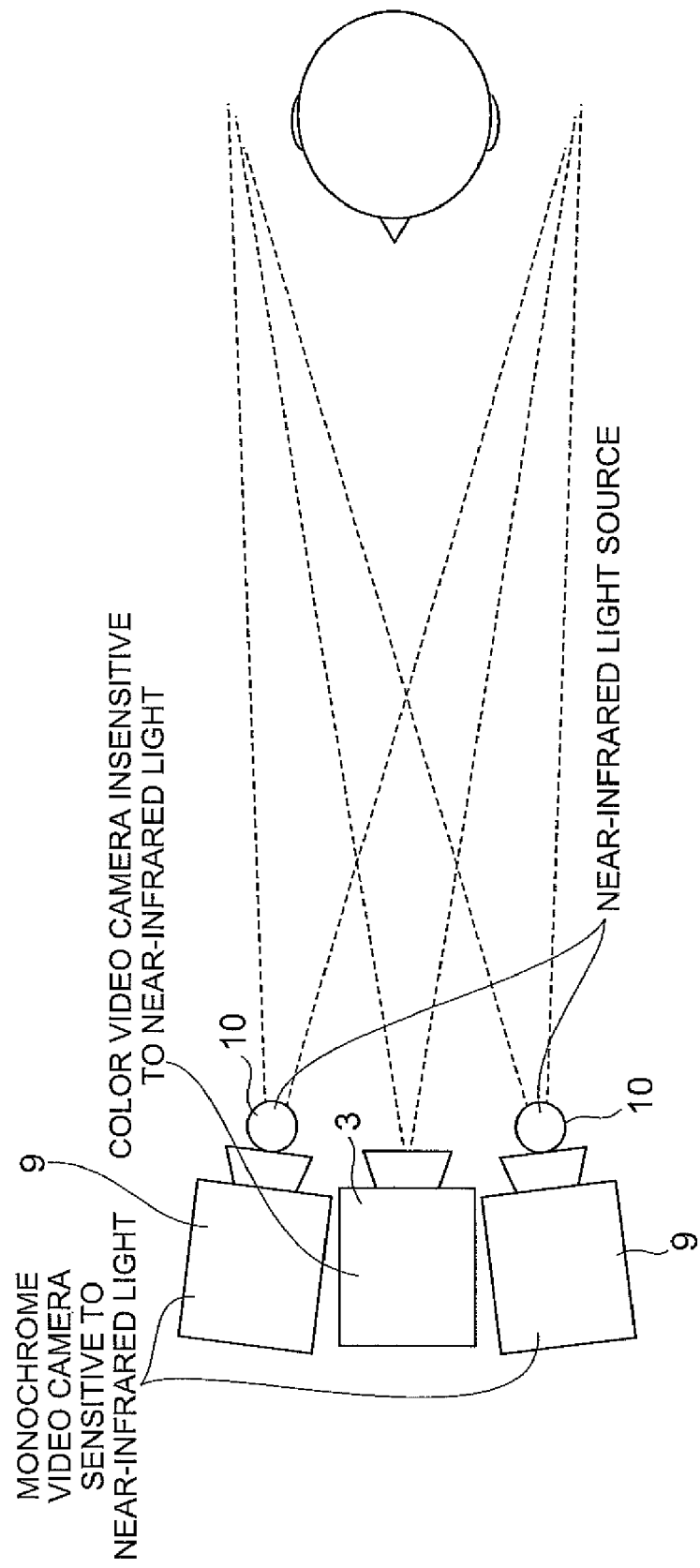
FIG. 2 is a plan view showing placement of a color video camera for image capturing a face of a mother and an optical system for detecting a pupil position of the mother.

The color camera 3 for photographing the image of the face of the mother, and a pupil position detection optical system 8 for measuring pupil coordinates that is included in the pupil position detection unit 4, are placed as in FIG. 2. The pupil position detection optical system 8 is a combination of infrared light-sensitive cameras (pupil detection cameras) 9 and near-infrared light sources 10. The pupil position detection unit 4 also includes a pupil position calculation unit 11, which detects a three-dimensional coordinate of each of the two pupils of the mother based on a stereo-calibrated output image from the pupil position detection optical system 8. The pupil position detection optical system 8 is placed close to where the color camera 3 for photographing the image of the face of the mother is placed.

Actually, a positional relationship between three cameras: two pupil detection cameras 9 and a color camera 3 is first determined and fixed so that all the cameras photograph approximately the same range on the face of the mother.

Then, camera calibration is performed. In the camera calibration, three degrees of freedom indicating the position of the camera center, three degrees of freedom indicating the rotation of the camera, the number of pixels of the image sensor of the camera, a value of an open area ratio (lens F-number), distortion of the camera system, and the like are simultaneously measured. In the camera calibration, it is supposed that there is a relationship in Expression 1 between a coordinate $(X_W, Y_W, Z_W)$ in a world coordinate system and a coordinate $(X_C, Y_C, Z_C)$ in a camera coordinate system of each camera, $$\begin{pmatrix} X_C \\ Y_C \\ Z_C \end{pmatrix} = R \begin{pmatrix} X_W \\ Y_W \\ Z_W \end{pmatrix} + T \quad \text{[Expression 1]}$$

and elements of a rotation matrix R and a translation vector T shown in Expression 2 are determined for each camera.

$$R = \begin{pmatrix} r_1 & r_2 & r_3 \\ r_4 & r_5 & r_6 \\ r_7 & r_8 & r_9 \end{pmatrix} \quad T = \begin{pmatrix} T_x \\ T_y \\ T_z \end{pmatrix} \quad \text{[Expression 2]}$$

The pupil position calculation unit 11 utilizes the above. The pupil position calculation unit 11 calculates the three-dimensional coordinates of the pupils in the world coordinate system through the pupil detection system including the two pupil detection cameras 9, and again assigns the coordinates to an expression for the color camera 3 corresponding to the (Expression 1), thereby calculating the coordinates of the pupils in the camera coordinate system of the color camera 3. The pupil position calculation unit 11 further converts the coordinates into coordinates in the image (converts the coordinates from a real unit system into a pixel unit system of the image) to determine the pupil positions of the mother. Alternatively, a camera calibration approach may be used in which the aforementioned world coordinate system is replaced with the camera coordinate system of the color camera 3 to determine camera calibration values for the other cameras in that camera coordinate system. In this case, the three-dimensional coordinates of the pupils determined by the two pupil detection cameras 9 are obtained as coordinates in the camera coordinate system of the color camera 3. The obtained coordinates are converted into coordinates in the color camera image to determine the pupil positions of the mother.

The data analysis unit 7 receives an input of an eye-gaze point coordinate of the infant from the eye-gaze point detection unit 2, and converts the eye-gaze point coordinate into a coordinate in the image video-captured by the color camera 3. Further, the data analysis unit 7 receives the coordinate of the pupil of the mother from the pupil position detection unit 4, performs various calculations using the eye-gaze point coordinate and the pupil position, and displays data on an external data display. Supposed calculations include, for example, calculating a deviation between the coordinate of the eye-gaze point and the pupil position, or displaying a locus of the eye-gaze point on the image of the mother, or the two dimensional distribution of the coordinate of the eye-gaze point on the coordinate of the pupil position.

According to the above-described autistic infant diagnosis apparatus 1 in the first embodiment, the eye-gaze point coordinate of the subject on the image displayed on the display 5 for is detected through image processing that uses processing of a differential between a bright pupil image and a dark pupil image. This enables immediate and reliable acquisition of the eye-gaze point coordinate. The burden on the subject is also lighter comparing with conventional head-mounted eye-gaze point detection devices. Further, the three-dimensional positions of the pupils of the observed target are similarly detected through image processing that uses processing of a differential between a bright pupil image and a dark pupil image, enabling speedup of the processing. From the three-dimensional positions of the pupils of the observed target, the coordinates of the pupils on the display 5 are calculated based on the camera calibration result, so that the relationship between the eye-gaze point coordinate of the subject and the pupil coordinates of the observed target is revealed. An image representing the relationship is further displayed on a data display for a doctor 12. This facilitates confirmation by a doctor or a medical technologist of correct acquisition of the data, and enables prompt and accurate autistic diagnosis for the subject. That is, the deviation of the eye-gaze point of the subject from the eye positions of the observed target can be immediately and easily visualized to enable acquisition of highly reliable diagnostic data about autism.

A moving image of the face of the observed target on which a dot (or something like a mouse cursor) indicating the eye-gaze point position of the subject is superimposed, or relevant quantified data, may be shown to the infant's mother on the display 5 or on the data display for a doctor 12 immediately after the examination or by calling back the mother when suspected autism is diagnosed. Generally, an infant diagnosed as autism is to be provided with suitable remedial education, and for this purpose, the mother's understanding (recognition that her own child is autistic) is important. These image and quantified data are also used as materials for prompting such understanding.

Conventional eye-gaze point detection devices (for example, eye trackers of Tobii Technology) can measure a response to displayed video by detecting an eye-gaze point on a screen. However, these devices cannot detect an eye-gaze point of a subject and pupil positions of an observed target accompanying the subject while an image of the observed target is captured with a camera and video of the observed target is displayed on a display, as in the present invention. In this embodiment, the three-dimensional positions of the pupils of the observed target are detected and subjected to the coordinate conversion to enable immediate simultaneous detection of the eye-gaze point of the subject and the pupil positions of the observed target. Since the eyeball shape generally varies with the subject, eye-gaze point calibration needs to be performed for an eye-gaze point detection device. Conventional eye-gaze point detection devices require the subject to gaze at many (for example, five) calibration points on the display, but it is difficult to cause the subject to accurately gaze at many calibration points if the subject is an infant. This inventor has proposed calibrating methods such as a method requiring gazing at no particular calibration points, a method requiring gazing at only one calibration point, and a method requiring gazing at two calibration points in Japanese Patent Applications Nos. JP 2010-274074 and JP 2010-178782, and these methods can be used in this application.

Embodiment 2

Figure 3:
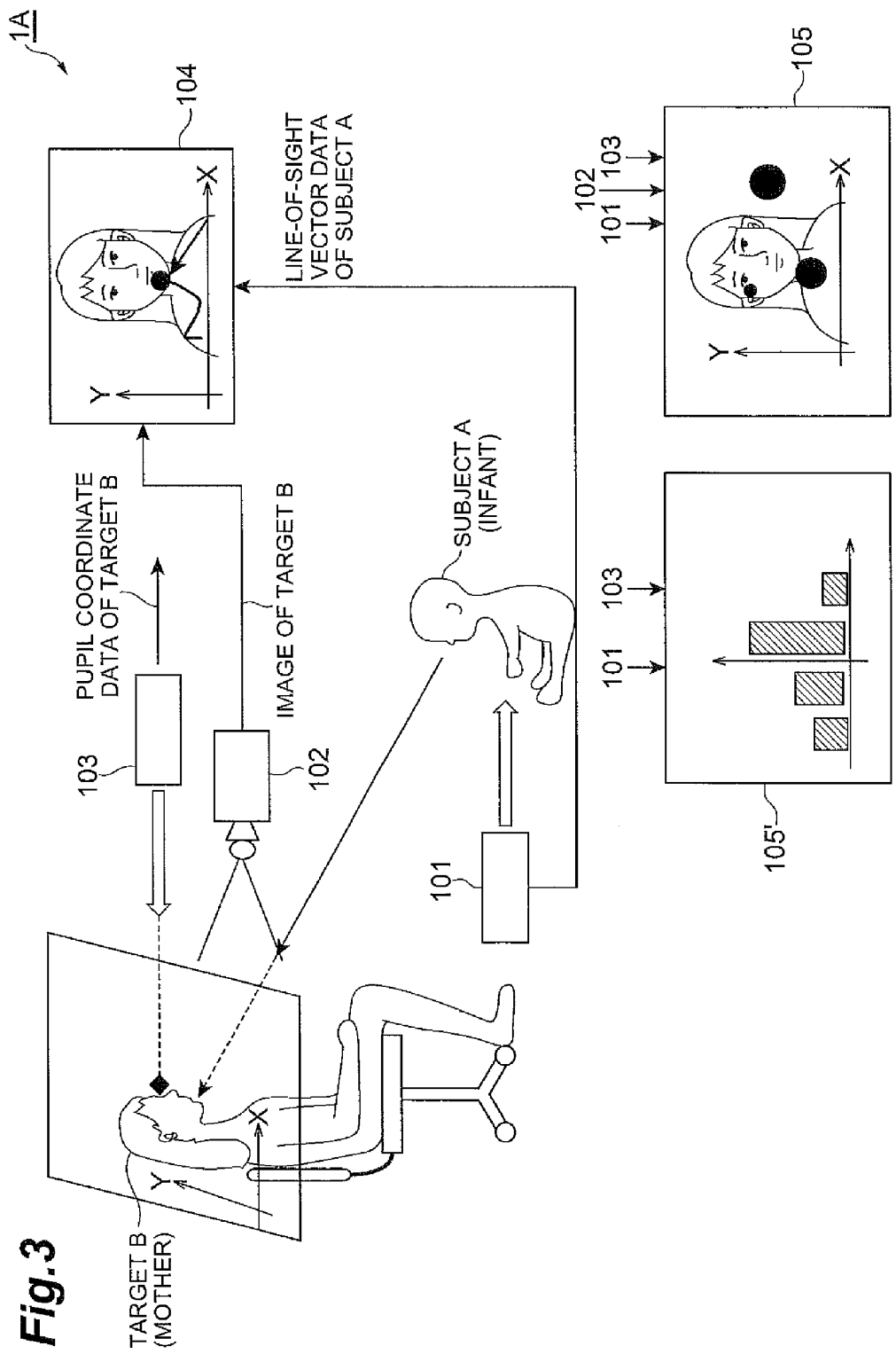
FIG. 3 is a schematic configuration diagram showing an autistic infant diagnosis apparatus in a second embodiment of the present invention.

FIG. 3 shows a configuration of a second embodiment of the present invention. The autistic infant diagnosis apparatus 1A according to the second embodiment of the present invention relates to a system that measures a line-of-sight direction and an eye-gaze position of a subject A relative to a person or an object (hereinafter collectively referred to as an observed target B) and also detects three-dimensional pupil positions and a line-of-sight direction of the observed target B.

It is assumed here that the mother and the infant in the first embodiment are the observed target B and the subject A, respectively.

The autistic infant diagnosis apparatus 1A includes a line-of-sight vector detection unit (a line-of-sight detection unit) 101 (for example, a "three-dimensional view-point measurement device" disclosed in U.S. Pat. No. 7,533,989 by this inventor is used) that measures a line-of-sight vector of the subject A, a camera 102 that takes an image of the observed target B looked at by the subject A, a pupil coordinate detection unit (a pupil position detection unit) 103 (for example, a "pupil detection device and a pupil detection method" disclosed in WO 2007/023798 by this inventor is used) that measures pupil coordinate points (three-dimensional positions of the pupils of the target B) and corneal reflection points and calculates a line-of-sight direction of the observed target B from the measurement result, an image display unit (an eye-gaze point detection unit, an eye-gaze point calculation unit) 104 that synthesizes and displays the coordinates and the image, and data display units (data analysis units) 105 and 105' that perform data analysis and display an analysis result.

The pupil coordinate detection unit 103 and the camera 102 employ a configuration as in FIG. 2. Specifically, the pupil coordinate detection unit 103 has two pupil detection systems as shown in FIG. 2. That is, the near-infrared light source 10 close to the camera 9 of one optical system and the near-infrared light source 10 close to the camera 9 of the other optical system are alternately turned on to obtain a bright pupil image and a dark pupil image of the observed target B, at each of the two pupil detection cameras 9. The pupil coordinate detection unit 103 determines a difference between the two images to detect pupil coordinates in the camera coordinate systems of the two cameras 9. At the same time, the pupil coordinate detection unit 103 uses the images from the two cameras 9 to detect coordinates of corneal reflection points in the respective camera coordinate systems. From the pupil coordinates in the coordinate systems of the two cameras 9, the pupil coordinate detection unit 103 calculates the three-dimensional coordinates of the two pupils of the observed target B in the world coordinate system. Further, from the pupil coordinates and the corneal reflection point coordinates in the coordinate systems of the two cameras 9, and the three-dimensional coordinates of the pupils in the world coordinate system, the pupil coordinate detection unit 103 further calculates line-of-sight vectors of the eyes of the observed target B, including the start points of the vectors. With this configuration of the pupil coordinate detection unit 103, the two three-dimensional pupil positions and the line-of-sight directions including the start points can be immediately and reliably detected for the observed target B.

The line-of-sight vector detection unit 101 may employ a configuration such that the color camera 3 is removed from the configuration in FIG. 2. In the same manner as the pupil coordinate detection unit 103, the line-of-sight vector detection unit 101 can immediately and reliably calculate line-of-sight vectors of the eyes of the subject A, including the start points of the vectors.

The image display unit 104 calculates an eye-gaze point coordinate by finding an intersection between the line-of-sight vector of the subject A measured by the line-of-sight vector detection unit 101 and a coordinate plane including the pupil coordinate point of the observed target B. Then, the image display unit 104 synthesizes and displays on a display, the calculated coordinate, an image of the observed target B video-captured by the camera 102, and a movement locus of the eye-gaze point coordinate of the subject A. The "coordinate plane" is a virtual plane set near a face of the observed target B and perpendicular to an optical axis of the camera 102.

The data display units 105 and 105' calculates a distance between the pupil coordinate point of the observed target B measured by the pupil coordinate detection unit 103 and the eye-gaze point coordinate of the subject A, and frequency per unit time of the eye-gaze point coordinate of the subject A. Then, the data display units 105 and 105' outputs to a display (and data recording devices such as printers) the calculated distance and the calculated frequency with a histogram or a size of a circle simultaneously with displaying by the image display unit 104. The data display unit 105' may calculate a relative distance $d_1$ from the eye-gaze point to the right pupil and a relative distance $d_2$ from the eye-gaze point to the left pupil using the equations:

$$d_1 = |G - P_1|$$

$$d_2 = |G - P_2|$$

where G is the eye-gaze point coordinate of the subject A on the coordinate plane, and $P_1$ and $P_2$ are the right and left pupil coordinate points of the observed target B on the coordinate plane, respectively. The data display unit 105' may then take the smaller one of the distances $d_1$ and $d_2$ as d to determine a frequency distribution of d and to calculate an average and a standard deviation of d, which may be displayed as evaluation values for autism diagnosis.

Figure 4:
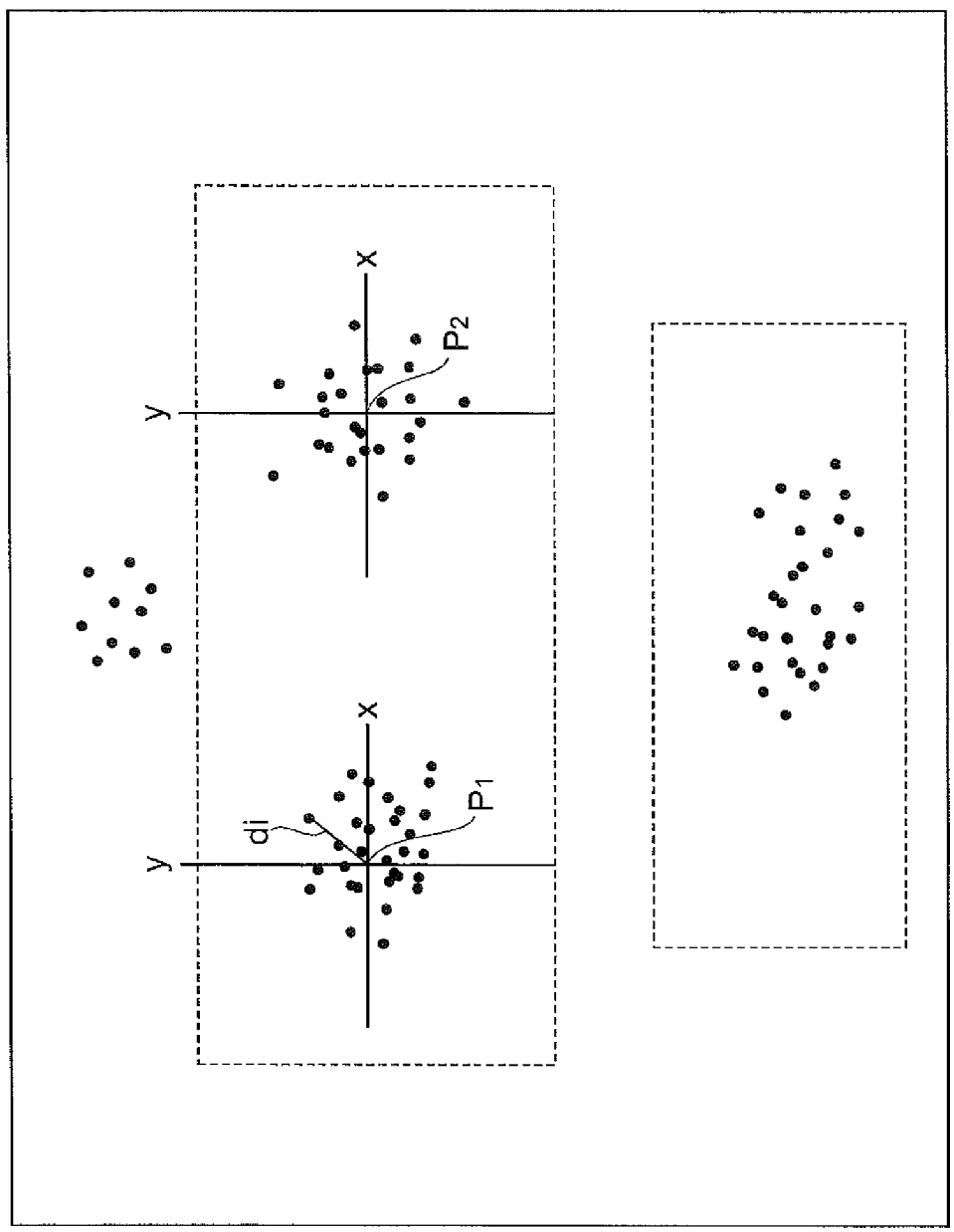
FIG. 4 is a diagram showing an exemplary display for autism diagnosis displayed by a data display unit in FIG. 3.

The data display unit 105' may plot and display the eye-gaze point coordinate G involving the smaller one of the distances $d_1$ and $d_2$ as a coordinate $G-P_1$ or $G-P_2$ with $P_1$ or $P_2$ being an origin (or convert the density of the coordinate points into a variable-density image) as shown in FIG. 4. Here, as shown by dotted lines in FIG. 4, the data display unit 105' may identify an eye area that reliably includes the eyes of the observed target B and a mouth area that reliably includes the mouth of the observed target B. The data display unit 105' may then count the following numbers: the number of moving image frames with the eye-gaze point coordinate G detected within the eye area, $Count_1$; the number of moving image frames with the eye-gaze point coordinate G detected within the mouth area, $Count_2$; the number of moving image frames with the eye-gaze point coordinate G detected outside the eye area, $Count_3$; and the total number of frames taken into account for the calculation, $Count_{tot}$. The data display unit 105' may calculate and display an autism index using the equation $$\text{autism index 1} = Count_1/Count_{tot}$$

or the equation $$\text{autism index 2} = Count_2/(Count_3+Count_2).$$

The autism index 1 indicates the probability of the eye-gaze point residing within the eye area, and the autism index 2 indicates the degree of tendency of looking at the mouth. Outputting such an index is very effective for autism diagnosis because an autistic infant tends to look at parts of an opposite person other than the eyes, especially parts such as the mouth that moves as the person speaks.

Instead of displaying the relationship between the eye-gaze point position of the subject A and the pupil positions of the observed target B, the data display unit 105' may display a relationship between the simultaneously detected line-of-sight vectors of the both persons. For example, the data display unit 105' may calculate an average and a standard deviation of a misalignment between the moving directions of the line-of-sight vectors of the both persons and may display the calculated values as evaluation values for autism diagnosis. A healthy person has a nature of almost reflectively looking toward the direction of the line of sight of an opposite person in front of the healthy person when the opposite person suddenly turns the eyes to a certain direction. An autistic patient lacks this nature and therefore tends to less responsive to a movement of an opposite person's line of sight. Outputting the correlation of the movements of the line-of-sight vectors as evaluation values in this manner provides an effective criterion for autism diagnosis.

According to the above-described autistic infant diagnosis apparatus 1A in the second embodiment, the two three-dimensional pupil positions and the line-of-sight vectors including the start points can be immediately and easily detected for the observed target B. Also, the line-of-sight vectors of the eyes of the subject A including the start points are calculated, so that the eye-gaze point of the subject A on the coordinate plane that includes the pupils of the observed target B for the subject A are immediately and reliably calculated. Particularly, by detecting the three-dimensional positions of the pupils of the observed target B and the line-of-sight vectors including the start points of the subject A, the eye-gaze point of the subject A on the virtual plane can be calculated in a simple manner with reduced constraints in making a diagnosis with the both persons facing each other. Since the subject A is especially intended to be an infant, it is very advantageous for smooth examination that there is no need to fix the posture or the head position of the subject A. Also, the values obtained from the relationship between the eye-gaze point position of the subject A and the pupil positions of the observed target B, and the values obtained from the correlation of the movements of the line-of-sight vectors of the both persons can be simultaneously and immediately output as evaluation values for autistic diagnosis.

Variation 1

Figure 5:
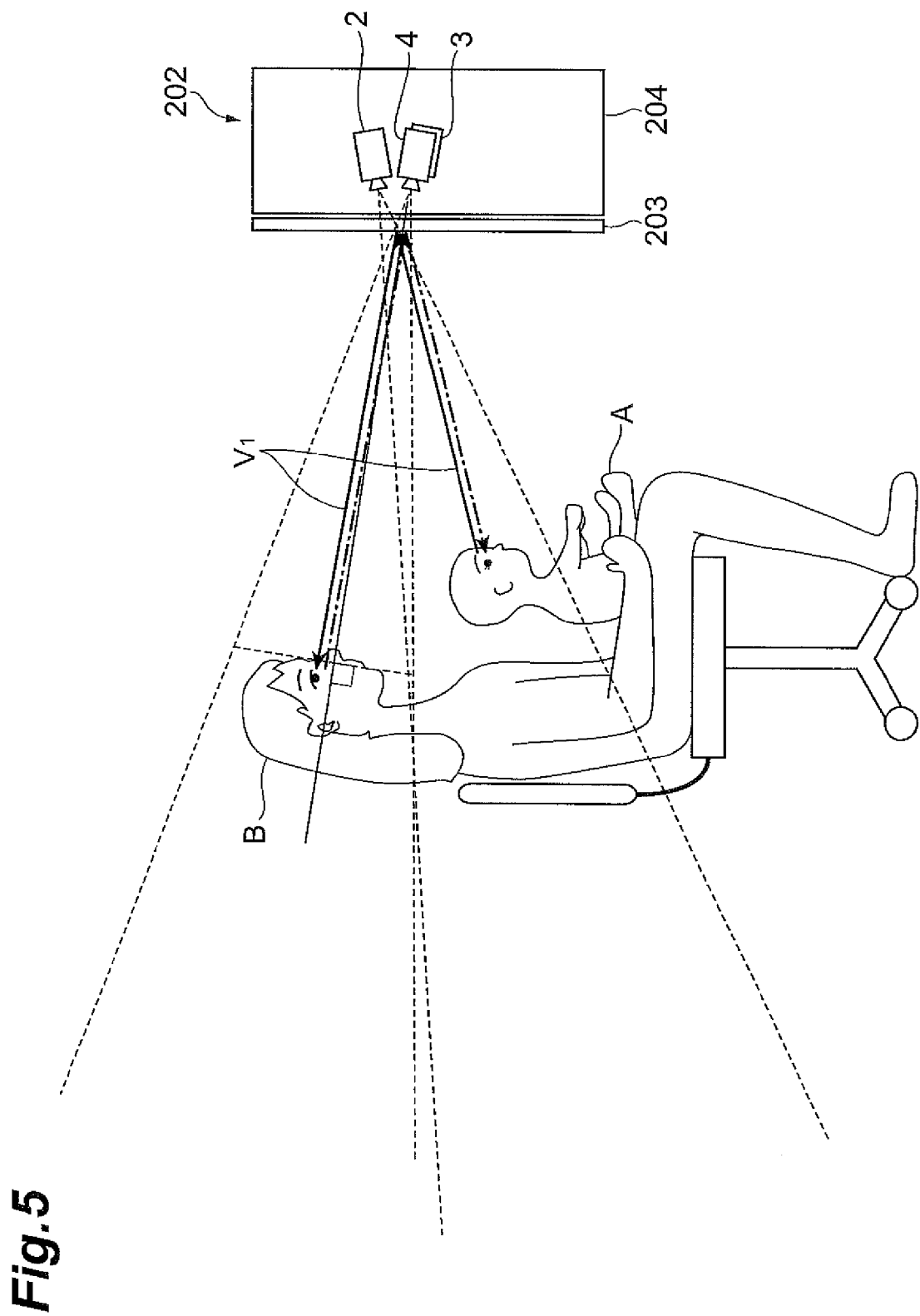
FIG. 5 is a diagram showing an optical system configuration according to a variation of the present invention.

FIG. 5 shows a configuration of a variation of the present invention. An autistic infant diagnosis apparatus according to the first variation of the present invention is a variation with respect to the optical system configuration that includes the cameras and the light sources in the second embodiment. This variation facilitates addressing the problem of difficulty in fixing the subject A and allows hiding devices such as cameras from the subject A to prevent the attention of the subject A from being attracted by the devices such as the cameras.

As shown in FIG. 5, an optical system 202 in this variation includes a flat magic mirror 203 and a shielding box 204 having a shape that surrounds the edges of the magic mirror 203, as well as a color camera 3, a pupil position detection unit 4, and an eye-gaze point detection unit 2 that are placed inside the shielding box 204 and have the same configurations as in the first embodiment.

The color camera 3 and the pupil position detection unit 4, configured as shown in FIG. 2, capture a color moving image of the face of the observed target B while detecting the three-dimensional positions of the pupils of the observed target B. The color camera 3 and the pupil position detection unit 4 are positioned to be directed to the observed target B through the magic minor 203. The eye-gaze point detection unit 2 is positioned to be directed to the subject A through the magic mirror 203 and detects the line-of-sight vectors of the subject A.

The magic mirror 203 is a beam splitter used for applications such that it appears as a mirror from a bright side but allows the bright side to be seen through it from the other dark side. For example, a half mirror with an equal optical transmittance-reflectance ratio is used as the magic mirror 203.

With this optical system 202, from the subject A, the devices such as the cameras and the light sources are not seen whereas the observed target B seems to face the subject A due to a reflected image of the observed target B. Also, stereo calibration (calibration using camera positions and directions in the world coordinate system, and internal parameters of the cameras) can be performed for all the cameras included in the color camera 3, the pupil position detection unit 4, and the eye-gaze point detection unit 2 to convert one camera coordinate system into another. By this conversion, data can be captured as if the subject A and the observed target B are facing each other.

Accordingly, in the autistic infant diagnosis apparatus in this variation, a line-of-sight vector $V_1$ from a pupil of the subject A toward the face of the observed target B can be converted into a vector in the coordinate system of the color camera 3 used for capturing the observed target B. An intersection of the line-of-sight vector $V_1$ and an image-capturing plane of the color image can be set as the eye-gaze point of the subject A, and then the eye-gaze point superimposed on the color image of the face of the observed target B can be displayed. The image-capturing plane of the color image herein is, for example, a plane that passes through the midpoint between the two pupil positions determined by the pupil position detection unit 4 and that is perpendicular to the optical axis of the color camera 3. Thus, the autistic infant diagnosis apparatus in this variation can determine, as the eye-gaze point position, the midpoint between intersections of the line-of-sight vectors of the eyes of the subject A with the image-capturing plane, and can display eye-gaze point data superimposed on the moving image of the face of the observed target B. Data as in the second embodiment may be selected as the data to be displayed.

What is claimed is:

1. An autism diagnosis support apparatus that detects a symptom of autism based on a state of a subject looking at a target, comprising:
    a line-of-sight detection unit that detects a line-of-sight direction of the subject looking at the target;
    a camera that takes an image of the target;
    a pupil position detection unit that measures a pupil coordinate of the target; and a data analysis unit that calculates a relationship between the line-of-sight direction of the subject and a pupil position of the target using the line-of-sight direction and the pupil coordinate and outputs the relationship along with the image of the target.

2. The autism diagnosis support apparatus according to claim 1, further comprising an eye-gaze point detection unit that calculates an eye-gaze point coordinate from a predetermined plane on which the target is seen and the line-of-sight direction, wherein the data analysis unit calculates a relationship between an eye-gaze point of the subject and the pupil position of the target using the eye-gaze point coordinate and the pupil coordinate and outputs the relationship along with the image of the target.

3. The autism diagnosis support apparatus according to claim 2, wherein the eye-gaze point detection unit comprises:

a camera that takes an image of the subject;

the line-of-sight detection unit that detects the line-of-sight direction of the subject based on the image; and an eye-gaze point calculation unit that calculates the eye-gaze point coordinate of the subject on the predetermined plane based on the line-of-sight direction, wherein the pupil position detection unit further detects a line-of-sight direction of the target based on the pupil position of the target.

4. The autism diagnosis support apparatus according to claim 3, wherein the data analysis unit further calculates a relationship between the line-of-sight direction of the subject and the line-of-sight direction of the target.

5. The autism diagnosis support apparatus according to claim 3, wherein the pupil position detection unit calculates the pupil coordinate of the target based on a bright pupil image and a dark pupil image of the target and detects the line-of-sight direction of the target using the pupil coordinate and a corneal reflection position of the target.

* * * * *